(12) United States Patent
Lee et al.

(10) Patent No.: US 12,156,923 B2
(45) Date of Patent: Dec. 3, 2024

(54) HYDROGEL PATCH INCLUDING ADDITIVE SOLUTION ADJUSTABLE FOR ITS SYNERESIS PATTERN AND METHOD OF MANUFACTURING THE COMPOSITION

(71) Applicant: Jincostech Co., Ltd., Siheung-si (KR)

(72) Inventors: Won Jin Lee, Siheung-si (KR); Jeong Pyo Lee, Siheung-si (KR)

(73) Assignee: JINCOSTECH CO., LTD., Siheung-si (KR)

( * ) Notice: Subject to any disclaimer, the term of this patent is extended or adjusted under 35 U.S.C. 154(b) by 632 days.

(21) Appl. No.: 17/510,162

(22) Filed: Oct. 25, 2021

(65) Prior Publication Data

US 2022/0151881 A1 May 19, 2022

Related U.S. Application Data

(63) Continuation of application No. PCT/KR2021/006650, filed on May 28, 2021.

(30) Foreign Application Priority Data

Nov. 19, 2020 (KR) ........................ 10-2020-0155170

(51) Int. Cl.
| | |
|---|---|
| *A61K 8/02* | (2006.01) |
| *A61K 8/04* | (2006.01) |
| *A61K 8/34* | (2006.01) |
| *A61K 8/365* | (2006.01) |
| *A61K 8/44* | (2006.01) |

(Continued)

(52) U.S. Cl.
CPC ............ *A61K 8/0208* (2013.01); *A61K 8/042* (2013.01); *A61K 8/345* (2013.01); *A61K 8/365* (2013.01); *A61K 8/44* (2013.01); *A61K 8/73* (2013.01); *A61K 8/731* (2013.01); *A61K 8/737* (2013.01); *A61K 8/9717* (2017.08); *A61Q 19/00* (2013.01)

(58) Field of Classification Search
None
See application file for complete search history.

(56) References Cited

FOREIGN PATENT DOCUMENTS

| | | |
|---|---|---|
| JP | 10150933 | 6/1998 |
| JP | 2002300854 | 10/2002 |

(Continued)

OTHER PUBLICATIONS

International Search Report—PCT/KR2021/006650 dated Aug. 31, 2021.

*Primary Examiner* — Kyung S Chang
(74) *Attorney, Agent, or Firm* — CANTOR COLBURN LLP

(57) ABSTRACT

Provided are a hydrogel patch, which controls syneresis of a hydrogel so as to enhance transdermal delivery of an active ingredient and has good physical properties, and a preparation method therefor. The hydrogel patch contains: a hydrogel composed of a mixture of phase A consisting of a crosslinking agent and purified water, phase B consisting of an organic polymer and a polyhydric alcohol, and phase C consisting of a pH adjusting agent and purified water; and a filling solution composed of a mixture of phase D consisting of a humectant and purified water, phase E consisting of a thickener and a polyhydric alcohol, and phase F consisting of a pH adjusting agent and purified water. The hydrogel of composition A is filled with the filling solution of composition C, and the hydrogel of composition B is filled with the filling solution of composition D.

7 Claims, 2 Drawing Sheets

(51) Int. Cl.
*A61K 8/73* (2006.01)
*A61K 8/9717* (2017.01)
*A61Q 19/00* (2006.01)

(56) References Cited

FOREIGN PATENT DOCUMENTS

| | | |
|---|---|---|
| KR | 100853301 | 8/2008 |
| KR | 20120015783 | 2/2012 |
| KR | 20130035362 | 4/2013 |
| KR | 101462390 | 11/2014 |
| KR | 20170041946 | 4/2017 |
| KR | 102256234 | 5/2021 |

(a)

(b)

(a)

(b)

HYDROGEL PATCH INCLUDING ADDITIVE SOLUTION ADJUSTABLE FOR ITS SYNERESIS PATTERN AND METHOD OF MANUFACTURING THE COMPOSITION

TECHNICAL FIELD

The disclosure relates to a hydrogel patch and a method for preparing the same, and more particularly, to a hydrogel patch, which is applied to cosmetics and enhances transdermal delivery of an active ingredient by containing a filling solution capable of controlling a syneresis pattern associated with the internal osmotic pressure of a hydrogel, and a method for preparing the same.

BACKGROUND ART

Hydrogel is an organic polymer material containing water in the vacancies of the network structure thereof, and has a water content of 20 to 80% depending on the intended use thereof. Hydrogel is a soft material having excellent biocompatibility, can be easily formed into a shape suitable for use, and thus is used in various fields such as medicine, cosmetics, and implants. In particular, in the cosmetic field, hydrogel is used as a formulation that induces transdermal delivery of an active ingredient through syneresis occurring in the hydrogel. According to S. Boral (2009), Syneresis in agar hydrogel, and K. Xu (2008), Spontaneous volume transition of polyampholyte nanocomposite hydrogels based on pure electrostatic interaction, syneresis of hydrogel is due to the mechanical and chemical properties of the organic polymer constituting the hydrogel, and is caused by irregular contraction and relaxation of the organic polymer due to a change in the thermodynamic properties thereof.

Mechanical properties of an organic polymer include molecular weight, chain length, number of unsaturated bonds, and crosslinking density of the polymer, and the like, and chemical properties thereof include ionic balance, pH, temperature, the types of crosslinking agent and colloidal dispersion medium, and the like. The spontaneous change in the volume of the hydrogel network by external environmental changes in the above factors is referred to as an overshooting phenomenon. According to C. Li (2010), Overshooting Effect of Poly(Dimethylaminoethyl Methacrylate) Hydrogel, the swelling ratio of the poly(dimethylaminoethyl methacrylate) hydrogel changes depending on temperature, pH, and ion concentration, and the change in the swelling ratio is due to the change in the chain length of the organic polymer constituting the network structure.

Various researches on controlling the syneresis pattern of hydrogel have been presented. Korean Patent Application No. 2007-0036270 discloses a hydrogel effective for maintaining water content by controlling the contents of iota carrageenan and locust bean gum, but does not specifically suggest improvement of the syneresis phenomenon occurring when the hydrogel is attached to the skin. Korean Patent Application No. 2012-0068886 discloses a temperature-sensitive hydrogel that undergoes syneresis near body temperature (37° C.) through photocrosslinking of Pluronic F68. However, according to the "Guidelines on Stability Testing of Cosmetic Products" notified by the Ministry of Food and Drug Safety, it is recommended that the thermal stability of hydrogel be evaluated at 40° C. or higher, because the hydrogel may be exposed to extreme temperature and pressure conditions. In addition, a temperature-sensitive hydrogel that undergoes syneresis in response to body temperature may undergo syneresis before attachment to the skin.

DISCLOSURE

Technical Problem

An object of the present disclosure is to provide a hydrogel patch, which controls syneresis of a hydrogel contained therein so as to enhance transdermal delivery of an active ingredient and has good physical properties such as gel formation, formulation stability, feeling of use, and the like so that the hydrogel patch is applied to cosmetics, and a method for preparing the same.

Technical Solution

To achieve the above object, the present disclosure provides a hydrogel patch containing a filling solution for controlling a syneresis pattern, the hydrogel patch containing: a hydrogel which is obtained by mixing together a phase A consisting of a crosslinking agent and purified water, a phase B consisting of an organic polymer and a polyhydric alcohol, and a phase C consisting of a pH adjusting agent and purified water, and is classified, according to the pH adjusting agent of the phase C, as a composition A having a neutral to basic pH and a composition B having an acidic pH; and a filling solution which is obtained by mixing together a phase D consisting of a humectant and purified water, a phase E consisting of a thickener and a polyhydric alcohol, and a phase F consisting of a pH adjusting agent and purified water, and is classified, according to the pH adjusting agent of the phase F, as a composition C having a neutral to basic pH or a composition D having an acidic pH. Here, the hydrogel of the composition A is filled with the filling solution of the composition C, and the hydrogel of the composition B is filled with the filling solution of the composition D.

In the hydrogel patch of the present disclosure, the pH adjusting agent may be arginine as a basic pH adjusting agent, or citric acid as an acidic pH adjusting agent. In the hydrogel patch composed of the composition A and the composition C, the composition A may be contained in an amount larger than 70% w/w based on the total weight of the hydrogel patch, and the composition C may be contained in an amount small than 30% w/w based on the total weight of the hydrogel patch. In the hydrogel patch composed of the composition B and the composition D, the composition B may be contained in an amount larger than 70% w/w based on the total weight of the hydrogel patch, and the composition D may be contained in an amount small than 30% w/w based on the total weight of the hydrogel patch.

In a preferred embodiment of the present disclosure, in the hydrogel, the crosslinking agent may be any one or a mixture of two or more selected from among cationic inorganic compounds containing an alkali metal salt or an alkaline earth metal salt, and the organic polymer may be one or more selected from among carrageenan, guar gum, carob gum, cellulose gum, and polyacrylate, and the polyhydric alcohol may be any one selected from glycerin, dipropylene glycol, butylene glycol, propanediol and pentylene glycol, or a combination of two or more thereof. The polyhydric alcohol may be a combination of glycerin and butylene glycol, and comprise, based on the total weight of the hydrogel, 5.0 to 20.0% w/w of glycerin and more than 0% w/w and less than or equal to 10.0% w/w of butylene glycol, and the combination may be contained in an amount of 15.0% w/w or more.

In the filling solution of the hydrogel patch of the present disclosure, the thickener may be one or more selected from among carbomer, xanthan gum, acrylate/C10-30 alkyl acrylate crosspolymer, ammonium acryloyldimethyltaurate/Vpi-copolymer, hydroxyethyl acrylate/sodium acryloyldimethyl taurate copolymer, hydroxyethyl cellulose, guar gum, carob gum, and cellulose gum, and the humectant may be one or a combination of two or more selected from the group consisting of allantoin, betaine, glucose, sorbitol, glycerin, butylene glycol, propanediol, and dipropylene glycol.

In a method for preparing a hydrogel patch containing a filling solution for controlling a syneresis pattern according to the present disclosure, a phase A consisting of a crosslinking agent and purified water, a phase B consisting of an organic polymer and a polyhydric alcohol, and a phase C consisting of a pH adjusting agent and purified water are stirred separately, and then the phase B and the phase C are sequentially added to the phase A, thus preparing a hydrogel. Thereafter, a phase D consisting of a humectant and purified water, a phase E consisting of a thickener and a polyhydric alcohol, and a phase F consisting of a pH adjusting agent and purified water are stirred separately, and then the phase E and the phase F are sequentially added to the phase D, thus preparing a filling solution. The hydrogel is filled with the filling solution.

In the method of the present disclosure, after the phase B is added to the phase A, the mixture may be stirred at 1,000 to 3,000 rpm and 70 to 95° C., and after the phase C is added to the phase A, the mixture may be stirred at 1,000 to 3,000 rpm and 70 to 95° C.

Advantageous Effects

In the hydrogel patch containing a filling solution for controlling a syneresis pattern and the method for preparing the same according to the present disclosure, the hydrogel patch is obtained by filling a hydrogel is filled with a filling solution for controlling a syneresis pattern so that the syneresis pattern of the hydrogel is controlled to enhance transdermal delivery of an active ingredient, and has good physical properties such as gel formation, formulation stability, feeling of use, and the like so that it is applied to cosmetics.

MODE FOR INVENTION

Figure 1:
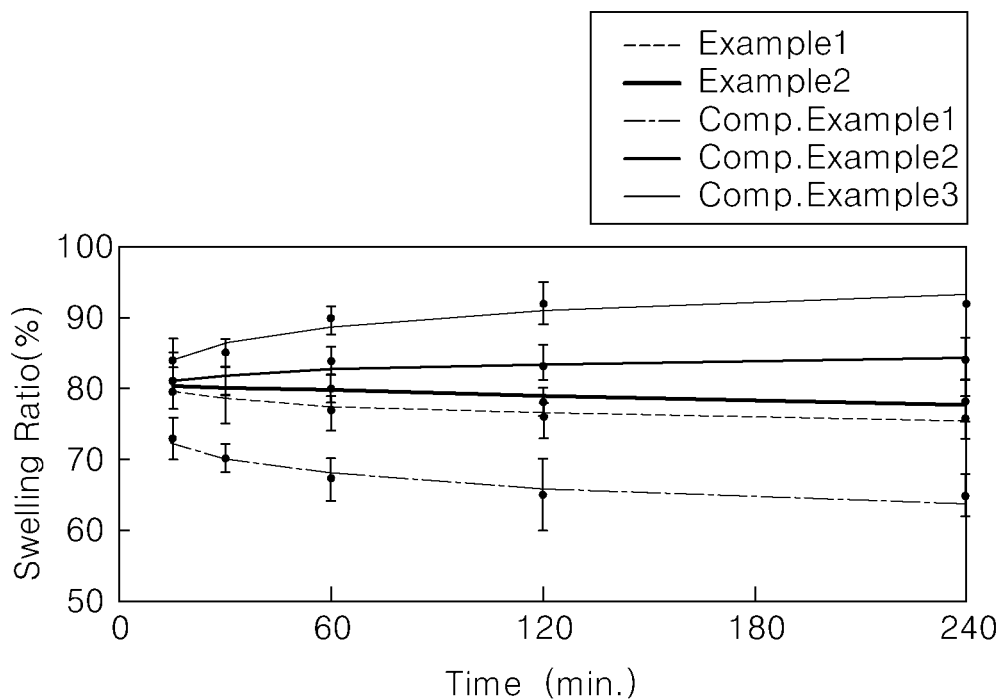
FIG. 1 is a graph showing time-dependent changes in the swelling ratios (%) of hydrogels in Examples 1 to 4 of the present disclosure and Comparative Examples 1 to 5.
Figure 1:
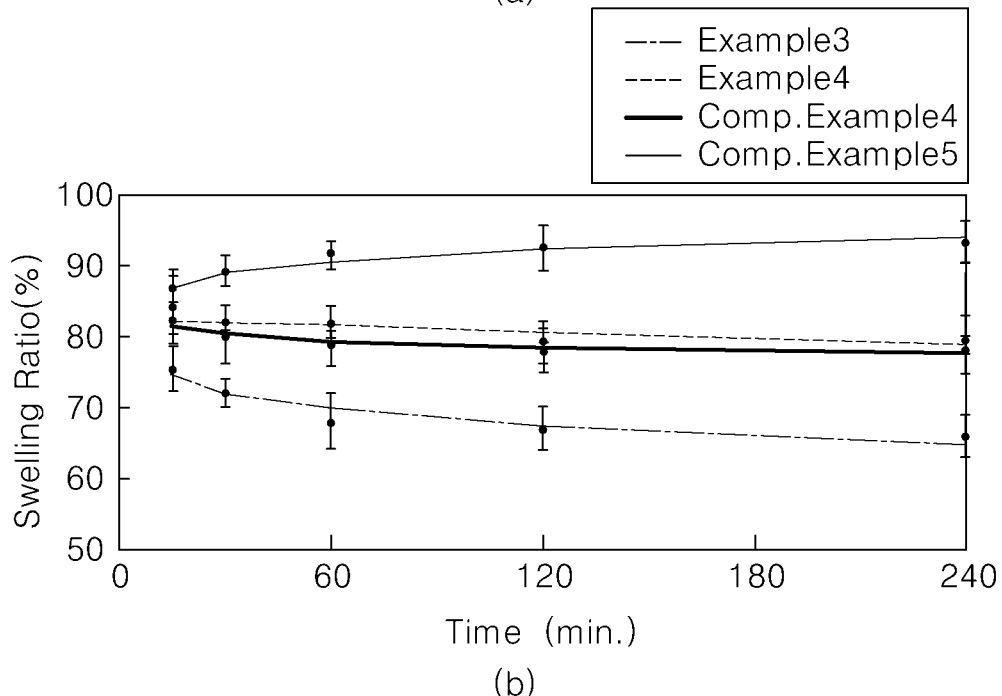

Hereinafter, preferred embodiments of the present disclosure will be described in detail with reference to the accompanying drawings. The embodiments described below may be modified in various different forms, and the scope of the present disclosure is not limited to the embodiments described in detail below. The embodiments of the present disclosure are provided to more completely explain the present disclosure to those of ordinary skill in the art.

Embodiments of the present disclosure provide a hydrogel patch, which is obtained by filling a hydrogel with a filling solution for controlling a syneresis pattern so that the syneresis pattern of the hydrogel is controlled to enhance transdermal delivery of an active ingredient, and has good physical properties such as gel formation, formulation stability, feeling of use, and the like so that the hydrogel patch is applied to cosmetics, and a method for preparing the same. To this end, a hydrogel and a filling solution filled therein will be described in detail, and the physical properties of the hydrogel patch filled with the filling solution will be described in detail. Here, the syneresis pattern is related to the internal osmotic pressure of the hydrogel, and is also referred to as a syneresis phenomenon. Hereinafter, a hydrogel patch filled with a filling solution for controlling the syneresis pattern and a method of preparing the hydrogel patch will be described separately.

<Hydrogel Patch Filled with Filling Solution for Controlling Syneresis Pattern>

The hydrogel according to an embodiment of the present disclosure contains a crosslinking agent, a polyhydric alcohol, an organic polymer, a humectant, a thickener, a pH adjusting agent, purified water, and other additives. The crosslinking agent induces ionic crosslinking in the organic polymer. The ionic crosslinking is achieved by electrostatic interaction between an ionized alkali metal or alkaline earth metal and COO— and OH—, which are anionic functional groups of the organic polymer.

The crosslinking shows an organic polymer having a network structure in purified water, and water is incorporated into the vacancy of the network structure to form a hydrogel. In order to stably provide crosslinking ionic species to the hydrogel, an alkali metal salt or an alkaline earth metal salt is preferably used. The counter ion of the alkali metal salt or alkaline earth metal salt affects the organic polymer and crosslinking. The counter ion is preferably chlorine salt, lactate, carbonate, or oxalate in consideration of the reaction thereof with the organic polymer, the ionic strength thereof, and the like.

The crosslinking agent is preferably calcium chloride. The solubility of calcium chloride in water is 74.5 g/100 ml (an anhydrous basis), suggesting that calcium chloride is stably dissolved in an aqueous solution. In addition, since the chlorine ion that is used as the counter ion does not react with the organic polymer, it is suitable as a crosslinking agent for preparing a stable hydrogel composition. The content of the crosslinking agent is more than 0% w/w and less than or equal to 5.0% w/w, preferably 0.1 to 0.2% w/w, based on the weight of the hydrogel. If the content of the crosslinking agent is more than 5.0% w/w, the hydrogel is not flexible, is broken due to brittleness thereof, and shows a dry feeling upon use. The content of the crosslinking agent may change depending on the type, number of functional groups, degree of polymerization, and content of the organic polymer.

The polyhydric alcohol changes the rheological structure of the organic polymer by wetting the organic polymer. The hydrodynamic radius ($\alpha$) of the organic polymer is determined according to the affinity between the organic polymer and the solvent. The solvent is classified as a good solvent in the case of $\alpha>1$, a theta ($\theta$) solvent in the case of $\alpha=1$, and a poor solvent in the case of $\alpha<1$. In order to achieve the chain structure of the hydrogel, it is preferable that the polymer is swollen in the good solvent or theta ($\theta$) solvent and then subjected to crosslinking. When the poor solvent is used, the organic polymer becomes entangled due to the random coil behavior of the organic polymer, making it difficult to form a network structure. Accordingly, it is necessary to select an appropriate solvent to swell the organic polymer.

The polyhydric alcohol is preferably a combination of glycerin and butylene glycol. Specifically, the polyhydric alcohol comprise, based on the total weight of the hydrogel, 5.0 to 20.0% w/w of glycerin and more than 0% w/w and less than or equal to 10.0% w/w of butylene glycol, and the combination is contained in an amount of 15.0% w/w or more based on the total weight of the hydrogel. The glycerin has a high affinity for the organic polymer, and the butylene glycol has a lower affinity than the glycerin. The hydrodynamic radius of the mixed solution obtained by combining the two solvents may be adjusted in consideration of the affinity of the organic polymer. In addition, if the total content of the organic solvents is less than 15.0% w/w, the concentration of the organic polymer becomes excessively high. If the concentration becomes excessively high, the repulsive force due to van der Waals force of each organic polymer species and the vacancy thereof are insufficient. For this reason, even when an organic solvent having high affinity is used, it shows the random coil behavior, and thus is not suitable for hydrogel reaction.

The organic polymer includes carrageenan and carob gum, and in some cases, may include at least one selected from among xanthan gum, guar gum, gellan gum, cellulose gum, agar, polyacrylamide, polyvinyl alcohol, polyacrylate, and polydimethylsiloxane. Meanwhile, the crosslinking of the organic polymer is classified into physical bonding and chemical bonding. The physical bonding is formed by entanglement due to van der Waals force of the chain polymer. The chemical bonding mainly occurs while the crosslinking agent combines with the organic polymers. The chemical bonding may be classified into ionic crosslinking by electrostatic interaction of ionic species, and covalent crosslinking by substitution, condensation or radical reaction between crosslinking chemical species and the functional groups of organic polymers.

The carrageenan is a natural polymer extracted from red algae, and is composed of calcium sulfate, sodium sulfate, potassium sulfate, magnesium sulfate and ammonium sulfate esters of galactose and 3,6-galactose anhydride copolymers. These sulfate ester functional groups are highly electrostatically strongly negative compared to other inorganic sulfate salts. The carrageenan may be classified into λ, κ, ι, ε, and μ types according to the position of the functional group, and κ-carrageenan and ι-carrageenan form a gel by crosslinking with potassium and calcium, respectively. λ-carrageenan does not undergo a gelation reaction due to the structural characteristics of α-helix thereof. [Necas, Jiri, and Ladislava Bartosikova. "Carrageenan: a review." Veterinarni medicina 58.4 (2013)]. The carrageenan is a component contributing to the stiffness of the hydrogel, and is contained in an amount of 0.1 to 5.0% w/w, preferably 1.0 to 3.0% w/w, based on the total weight of the hydrogel. If the content of the carrageenan is less than 0.1% w/w, the basic stiffness required for gel formation is not achieved, and if the content of the carrageenan is more than 5.0% w/w, the brittleness of the gel becomes stronger, and thus a phenomenon occurs in which the gel breaks.

The carob gum is extracted from soybeans, and is a galactomannan with a level of substitution of one part mannose with four parts of galactose, and there is a non-random distribution of galactose side chains along the mannan backbone. The mannose-free regions of carob gum that are able to associate with the helical structures help form a gel by reaction with agar, κ-carrageenan or xanthan gum at high temperatures, and the carob gum does not form a gel by itself and forms crosslinks with citric acid in the presence of a sulfuric acid catalyst at high temperatures. [Hadinugroho, Wuryanto, et al. "Study of Catalyst of Citric Acid Crosslinking on Locust Bean Gum." Journal of Chemical Technology and Metallurgy 52.6 (2017): 1086-1091.].

The carob gum is used as a co-gelling agent to promote the gelation reaction of the carrageenan, and is contained in an amount of 0 to 4.0% w/w, preferably 1.0 to 3.0% w/w, based on the total weight of the hydrogel. If the content of the carob gum is more than 4.0% w/w, a hydrogel formulation may be obtained, but the viscosity of the syneresis may increase due to the nature of the galactomannan-based polymer. If the viscosity increases, an unpleasant feeling of use may occur when the hydrogel comes in contact with the skin.

The guar gum is mainly extracted from legumes, and is a polysaccharide composed of galactose and mannose. The backbone thereof is a linear chain of β-1,4-linked mannose residues to which galactose residues are 1,6-linked at every second mannose, forming side-branches. Structurally, the guar gum is very similar to the carob gum and xanthan gum to be described later. The guar gum forms a nonionic colloid in aqueous solution and does not undergo a gel-forming reaction by itself. However, the gel-forming reaction may be induced by calcium. The guar gum is used as a gelling agent to promote the gelation reaction of carrageenan, and is contained in an amount of more than 0% w/w and less than or equal to 4.0% w/w, preferably more than 0% w/w and less than or equal to 2.0% w/w, based on the total weight of the hydrogel. If the content of the guar gum is more than 4.0% w/w, there is no problem in terms of gel formation, but the syneresis liquid of the hydrogel becomes slippery and the adhesion of the hydrogel is lowered.

The xanthan gum may be obtained by fermenting carbohydrates with *Xanthomonas campestris*, and is a long-chain polysaccharide composed of D-glucose, D-mannose, and D-gluconic acid. In addition, the xanthan gum does not undergo a gelation reaction by itself, forms a colloid in aqueous solution, has increased viscosity at a high concentration, and exhibits the hydrodynamic behavior of pseudoplastic flow. The xanthan gum may be used as a substitute for guar gum, and may be used as a substitute for carrageenan to form a hydrogel network structure in the presence of a calcium crosslinking agent. The content of the xanthan gum is 0 to 5.0% w/w, preferably 0 to 2.0% w/w, based on the total weight of the hydrogel. If the content of the xanthan gum is more than 5.0% w/w, when calcium ions are used as a crosslinking agent, the brittleness of the hydrogel becomes stronger at 4.0% w/w or more, and thus the gel collapses and breaks when it is attached to the skin.

The cellulose gum is also called carboxymethyl cellulose (CMC), and is a cellulose derivative in which a carboxymethyl functional group (—CH2-COOH) is bonded to the hydroxyl group of glucose constituting the main chain of cellulose. The cellulose gum does not form a gel by itself and has the effect of increasing the viscosity of the syneresis liquid. The content of the cellulose gum is more than 0% w/w and less than or equal to 3.0% w/w, preferably more than 0% w/w and less than or equal to 2.0% w/w, based on the total weigh of the hydrogel. If the content of the cellulose gum is more than 3.0% w/w, gel formation may be achieved, but a phenomenon occurs in which the syneresis liquid is absorbed into the skin, remains on the skin, and is pushed out like dead skin.

The humectant may be one or a combination of two or more selected from the group consisting of allantoin, betaine, glucose, sorbitol, glycerin, butylene glycol, propanediol, and dipropylene glycol.

The allantoin is a component in which glycolic acid is substituted with diurea salt. The allantoin is effective in exfoliating dead epidermal cells of the outermost layer of the epidermis, and is widely used in cosmetics as a humectant that increases the water content of the extracellular matrix. The content of the allantoin is more than 0% w/w and less than or equal to 1.0% w/w, preferably more than 0% w/w and less than or equal to 0.5% w/w, based on the total weight of the filling solution. If the content of the allantoin is more than 1.0% w/w, the allantoin does not affect the formulation, but it is undesirably absorbed into the skin and a stiff feeling of use remains.

The thickener increases the viscosity of the filling solution and controls the osmotic pressure between the hydrogel and the filling solution, thereby controlling the syneresis patterns before and after skin attachment. The syneresis pattern of the hydrogel depends on the osmotic pressure and mass transfer coefficient of the hydrogel. The thickener increases the outside concentration of the hydrogel and reduces the osmotic pressure difference between the inside and the outside of the hydrogel structure, thereby reducing the naturally occurring syneresis of the hydrogel.

The thickener may be one or more selected from among carbomer, xanthan gum, acrylate/C10-30 alkyl acrylate crosspolymer, ammonium acryloyldimethyltaurate/Vpicopolymer, hydroxyethyl acrylate/sodium acryloyldimethyl taurate copolymer, hydroxyethyl cellulose, guar gum, carob gum, and cellulose gum. As this thickener, it is preferable to select a component having a chemical structure similar to that of the organic polymer constituting the hydrogel in order to eliminate the possibility of an unintended chemical reaction between the organic polymer and the thickener of the filling solution.

The content of the thickener is more than 0% w/w and less than or equal to 5.0% w/w, preferably more than 0% w/w and less than or equal to 1.0% w/w, based on the total weight of the filler solution. If the content of the thickener is more than 5.0% w/w, it becomes higher than the concentration of the hydrogel, so that the water of the hydrogel may move to the filling solution, which may cause a low water content of the hydrogel.

The pH adjusting agent adjusts the pH change caused by the reaction between the organic polymer and the crosslinking agent in aqueous solution and the reaction of the thickener in aqueous solution. As the pH adjusting agent, an appropriate acidic or a basic component is used so that the hydrogel have a suitable pH value for cosmetics.

According to the safety management standards notified by the Ministry of Food and Drug Safety, the pH range of commercial cosmetics is set to 3.0 to 9.0. However, since the hydrogel remains on the skin due to the nature thereof and continuously delivers the active ingredient to the skin, sensitive skin irritation by the pH occurs. That is, the appropriate pH range of the hydrogel is preferably 4.0 to 8.0. In addition, the chain length of the organic polymer changes depending on the pHs of the hydrogel and the filling solution, and thus the same hydrogel shows different syneresis patterns at different pHs.

In examples of the present disclosure, arginine was used as a basic pH adjusting agent, and citric acid was used as an acidic pH adjusting agent. The arginine is a basic amino acid and is widely used as a neutralizing agent in cosmetics, and the citric acid is a kind of $\alpha$-hydroxy acid and is mainly used to lower pH.

In addition to the components used in this embodiment, various additives may be used without limitation. The additives may include a flavoring agent, a colorant, a sequestering agent, and a skin conditioning agent.

<Method for Preparing Hydrogel Patch Filled with Filling Solution for Controlling Syneresis Pattern>

Hereinafter, methods for preparing the hydrogel and filling solution constituting the hydrogel patch will be described. In the process of preparing the hydrogel, a phase A consists of a crosslinking agent and purified water, a phase B consists of an organic polymer and a polyhydric alcohol, and a phase C consists of a pH adjusting agent and purified water. In the process of preparing the filling solution, a phase D consists of purified water and a humectant, a phase E consists of a thickener and a polyhydric alcohol, and a phase F consists of purified water and a pH adjusting agent. In other words, the phases A, B and C constitute the hydrogel, the phases D, E and F constitutes the filling solution. Accordingly, the phase A, phase B, phase C, phase D, phase E and phase F are each treated independently until they are mixed together to form the hydrogel and the filling solution.

In the method for preparing the hydrogel, raw materials were divided into the phases A, B and C which were then stirred separately, and then the phase B and the phase C were sequentially added to the phase A. Specifically, the phase A was stirred at 800 rpm and 85° C. for 5 minutes, the phase B was stirred at 800 rpm and room temperature for 5 minutes, and the phase C was stirred at 800 rpm and room temperature for 5 minutes. Thereafter, the phase B was added to the phase and then stirred at 1,000 to 3,000 rpm and 70 to 95° C. for about 5 minutes, and then the phase C was added thereto, followed by stirring at 1,000 to 3,000 rpm at 70 to 95° C. for about 5 minutes. A plastic film was coated with the high-temperature hydrosol to have a coating thickness of 0.1 to 5 mm by means of a roller, and then the coated hydrogel was cooled at a temperature of 1° C. to room temperature until the hydrogel reached room temperature, thus obtaining a hydrogel sheet. To measure the pH of the obtained hydrogel sheet, 4 g of the hydrogel was placed in 60 g of purified water and swollen sufficiently on a heating stirrer with a magnetic bar, followed by cooling to 25° C., and the pH of the cooled solution was measured using a pH meter.

After the phase B is added, the mixture may be stirred at appropriate rotation speed (rpm) selected depending on the weights of the organic polymer and polyhydric alcohol. However, if the stirring speed is lower than 1,000 rpm, the polymer is not properly dispersed and agglomerates, and if the stirring speed is higher than 3,000 rpm, excessive shear stress is applied to the chain organic polymer among the organic polymers and weakens the stiffness of the hydrogel, and the hydrogel spatters on the walls of the reactor and proper dispersion is not achieved. In addition, stirring after addition of the phase C is performed at lower than 1,000 rpm, uniform dispersion of the pH adjusting agent is not achieved due to the high viscosity of the hydrogel, and if the stirring is performed at higher than 3,000 rpm, the stiffness of the gel is weakened and proper dispersion is not achieved for the same reasons as described above with respect to the phase B.

In addition, if the coating thickness of the hydrogel is smaller than 0.1 mm, the hydrogel is easily torn due to the excessively small thickness thereof, and if the coating thickness is larger than 5 mm, the hydrogel easily slides off the skin due to the weight thereof, and thus the feeling of adhesion thereof is reduced. If the hydrogel is cooled to 0° C., the phase change from water to ice occurs and affects the stability of the hydrogel while expanding the volume of the hydrogel.

In the method for preparing the filling solution, raw materials were divided into the phases D, E and F which were then stirred separately, and then the phase E and the phase F were sequentially added to the phase D. Specifically, the phase D was stirred at 800 rpm and 80° C. for 5 minutes, the phase E was stirred at 800 rpm and room temperature for 5 minutes, and the phase F was stirred at 800 rpm and room temperature for 5 minutes. The phase E was added to the phase D and then stirred at 400 to 800 rpm at 80° C. for 5 minutes, and phase F was added thereto and then stirred at 400 to 800 rpm at 80° C. for 5 minutes, followed by cooling to room temperature. The pH of the resulting filling solution was measured using a pH meter.

After the phase E is added, the mixture may be stirred at appropriate rotation speed (rpm) selected depending on the weights of the phases D and E. However, if the stirring speed is lower than 400 rpm, the stirring is not done sufficiently, so that the thickener sinks to the bottom, and if the stirring speed is higher than 800 rpm, the filling solution spatters on the walls of the reactor and uniform dispersion is not achieved. In addition, stirring after addition of the phase F is performed at lower than 400 rpm, uniform dispersion of the phase F is difficult due to the viscosity of the filling solution, and if the stirring speed is higher than 800 rpm, the filling solution spatters on the walls of the reactor and uniform dispersion is not achieved. The cooling process may be freely selected from among air cooling, water cooling, and the like. When the filling solution is cooled to room temperature, the possibility of an unintended chemical reaction due to thermal imbalance between the hydrogel and the filling solution is eliminated.

Hereinafter, the following examples will be presented in order to describe the physical properties of the hydrogel of the present disclosure in detail. However, the present disclosure is not particularly limited to the following examples.

The prepared hydrogel was placed in a 78-mm-diameter container and formed into a circular shape having a diameter of 75 mm. At this time, the hydrogel was filled with the filling solution at the ratios described in Examples and Comparative Examples, and the change in swelling ratio of the hydrogel and the change in swelling ratio of the hydrogel after attachment to the skin were measured. The moisturizing feeling, adhesion, stiffness and stability of the hydrogel were evaluated by a panel group. The swelling ratio was calculated by the following equation 1.

$$SR = \frac{W - W_0}{W_0} \quad \text{[Equation 1]}$$

wherein
SR=swelling ratio;
W=weight (g) of hydrogel; and
$W_0$=dry weight (g) of hydrogel Table 1 below shows the components and their contents in hydrogel composition A and composition B and the pHs in order to explain the Examples of the present disclosure, and Table 2 below shows the components and their contents in hydrogel composition C and composition D and the pHs in order to explain the Examples of the present disclosure.

TABLE 1

| Phase | Component | Component A | Component B |
|-------|-----------|-------------|-------------|
| A | Purified water | To 100 | To 100 |
|   | Calcium chloride | 0.200 | 0.200 |
| B | Glycerin | 15.000 | 15.000 |
|   | Butylene glycol | 5.000 | 5.000 |
|   | Carrageenan | 2.000 | 2.000 |
|   | Carob gum | 1.000 | 1.000 |
|   | Guar gum | 0.500 | 0.500 |
|   | Cellulose gum | 0.500 | 0.500 |
| C | Purified water | 5.000 | 5.000 |
|   | Arginine | 0.060 | — |
|   | Citric acid | — | 0.010 |
|   | pH | 7.00 | 5.00 |

TABLE 2

| Phase | Component | Composition C | Composition D |
|-------|-----------|---------------|---------------|
| D | Purified water | To 100 | To 100 |
|   | Allantoin | 0.200 | 0.200 |
| E | Glycerin | 5.000 | 5.000 |
|   | Xanthan gum | 0.050 | 0.050 |
| F | Purified water | 5.000 | 5.000 |
|   | Arginine | 0.030 | — |
|   | Citric acid | — | 0.008 |
|   | pH | 7.00 | 5.00 |

The pH was in the range of 4 to 8 so as to satisfy the safety standards for commercial cosmetics notified by the Ministry of Food and Drug Safety. Specifically, the pHs of compositions A and C were set to 7, and the pHs of compositions B and D were set to 5.

Example 1

As the hydrogel of Example 1, composition A was prepared. According to each phase, phase A was stirred at 800 rpm and 85° C. for 5 minutes, phase B was stirred at 800 rpm and room temperature for 5 minutes, and phase C was stirred at 800 rpm and room temperature for 5 minutes. Next, phase B was added to phase A, followed by stirring at 2,000 rpm and 85° C. for 5 minutes, and then phase C was added thereto, followed by stirring at 2,000 rpm and 85° C. for 5 minutes. Thereafter, the resulting hydrogel was coated to a thickness of 2.0 mm, cooled to room temperature, and then formed into a circular shape having a thickness of 75 mm. As the filling solution of Example 1, composition C was prepared. According to each phase, phase D was stirred at 800 rpm and 80° C. for 5 minutes, phase E was stirred at 800 rpm and room temperature for 5 minutes, and phase F was stirred at 800 rpm and room temperature for 5 minutes. Next, phase E was added to phase D, followed by stirring at 500 rpm and 80° C. for 5 minutes, and then phase F was added thereto, followed by stirring at 500 rpm and 80° C. for 5 minutes. Thereafter, the resulting filling solution was allowed to cool down to room temperature in water at 4° C. In a process of filling the hydrogel of Example 1 with the filling solution, 90 g of the hydrogel was filled with 10 g of the filling solution in a circular container having a diameter of 78 mm.

Example 2

The procedure of Example 1 was repeated except that 80 g of composition A as a hydrogel was filled with 20 g of composition C as a filling solution in a circular container having a diameter of 78 mm.

Example 3

The procedure of Example 1 was repeated except that 90 g of composition B as a hydrogel was filled with 10 g of composition D as a filling solution.

Example 4

The procedure of Example 3 was repeated except that 80 g of composition B as a hydrogel was filled with 20 g of composition D as a filling solution.

Comparative Example 1

The procedure of Example 1 was repeated except that 100 g of composition A as a hydrogel was filled with no filling solution in a circular container having a diameter of 78 mm.

Comparative Example 2

The procedure of Example 1 was repeated except that 70 g of composition A as a hydrogel was filled with 30 g of composition C as a filling solution.

Comparative Example 3

The procedure of Example 1 was repeated except that 60 g of composition A as a hydrogel was filled with 40 g of composition C as a filling solution.

Comparative Example 4

The procedure of Example 1 was repeated except that 100 g of composition B as a hydrogel was filled with no filling solution.

Comparative Example 5

The procedure of Example 3 was repeated except that 70 g of composition B as a hydrogel was filled with 30 g of composition D as a filling solution.

Figure 2:
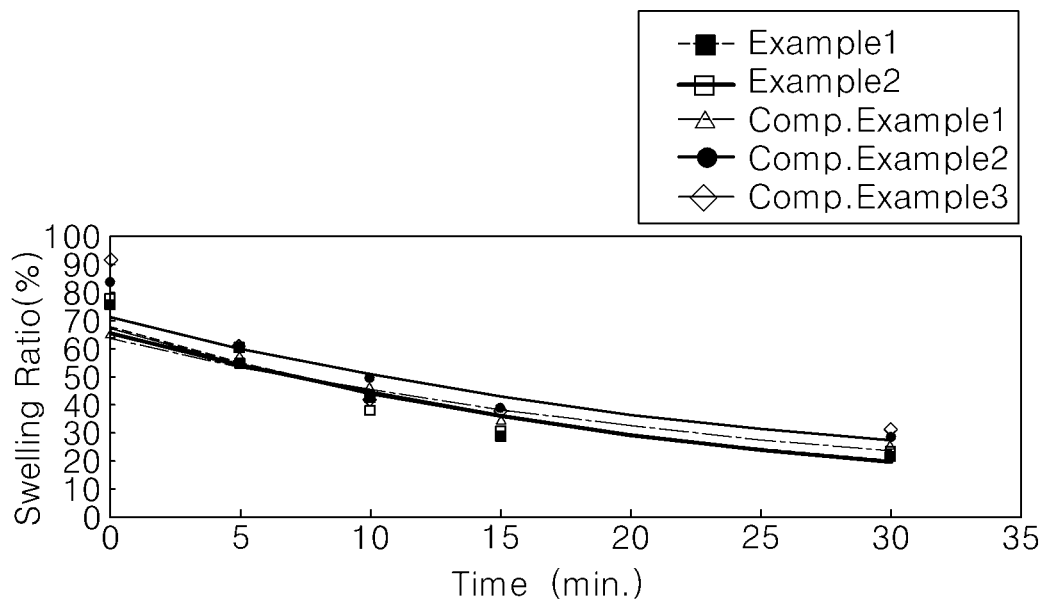
FIG. 2 is a graph showing time-dependent changes in the swelling ratios (%) of hydrogels in Examples 1 to 4 of the present disclosure and Comparative Examples 1 to 5 after attachment to the skin.
Figure 2:
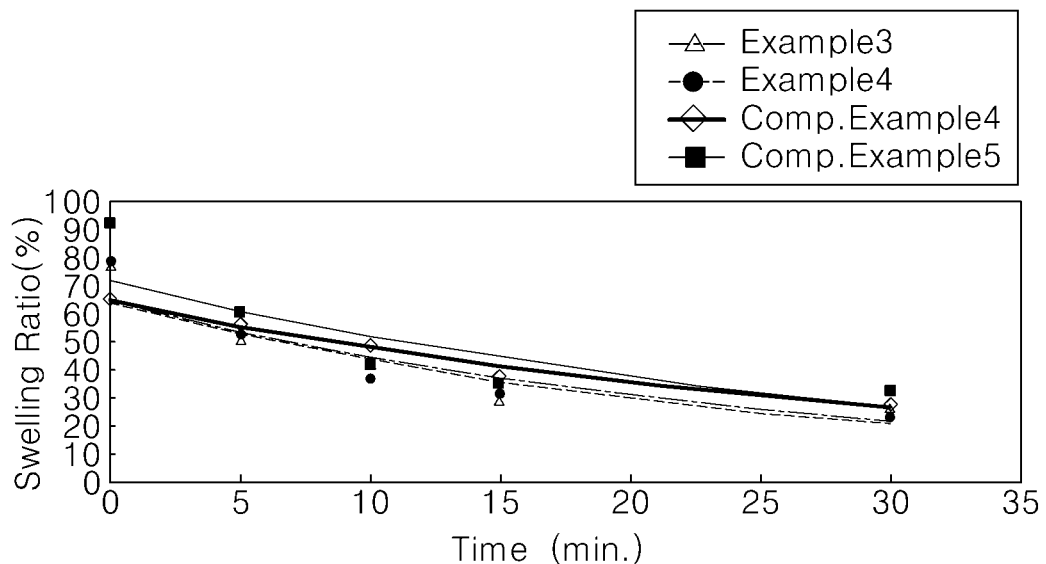

Table 3 below shows the physical properties of Examples 1 to 4 of the present disclosure and Comparative Examples 1 to 5. Here, the scores shown in Table 3 have the following means: 5: very good; 4: good; 3: moderate; 2: relatively unsuitable for use as cosmetics; and 1: not applicable to cosmetics. FIG. 1 is a graph showing time-dependent changes in the swelling ratios (%) of the hydrogels of Examples 1 to 4 of the present disclosure and Comparative Examples 1 to 5, and FIG. 2 is a graph showing time-dependent changes in the swelling ratios (%) of the hydrogels of Examples 1 to 4 of the present disclosure and Comparative Examples 1 to 5 after attachment to the skin.

|  | Example 1 | Example 2 | Example 3 | Example 4 | Comp. Example 1 | Comp. Example 2 | Comp. Example 3 | Comp. Example 4 | Comp. Example 5 |
|---|---|---|---|---|---|---|---|---|---|
| Composition A (%) | 90 | 80 | — | — | 100 | 70 | 60 | — | — |
| Composition B (%) | — | — | 90 | 80 | — | — | — | 100 | 70 |
| Composition C (%) | 10 | 20 | — | — | 0 | 30 | 40 | — | — |
| Composition D (%) | — | — | 10 | 20 | — | — | — | 0 | 30 |
| Moisturizing feeling | 4 | 5 | 5 | 5 | 3 | 5 | 5 | 4 | 5 |
| Adhesion | 5 | 5 | 5 | 5 | 4 | 3 | 2 | 3 | 2 |
| Stiffness | 5 | 4 | 4 | 4 | 5 | 3 | 2 | 4 | 2 |
| Stability | 5 | 4 | 4 | 3 | 3 | 3 | 2 | 4 | 2 |

Referring to Table 3 above, Example 1 exhibited very good adhesion, stiffness and stability and good moisturizing feeling. Example 2 exhibited very good moisturizing feeling and adhesion and good stiffness and stability. Example 4 exhibited very good moisturizing feeling and adhesion and good stiffness, but showed moderate stability.

Comparative Example 1 exhibited very good stiffness and good adhesion, but showed moderate moisturizing feeling and stability. In the case of Comparative Example 1 which included no filling solution, natural syneresis occurred due to the internal osmotic pressure of the hydrogel in the container, and thus the water content of the hydrogel decreased before skin application, thereby reducing the moisturizing feeling. In addition, the hydrogel was continuously exposed to a dry state, and the upper surface of the hydrogel showed an unstable form.

Comparative Example 2 exhibited a very good moisturizing feeling, but showed moderate adhesion, stiffness and stability. In the case of Comparative Example 2, the moisturizing feeling was improved by the filling solution, but due to an excessive amount of the filling solution, swelling of the hydrogel occurred as shown in FIG. 2, which had a negative effect on the gel stiffness and stability. In this case, when the hydrogel was applied to relatively dry skin, excessive syneresis of the hydrogel occurred, causing slippage of the hydrogel, and the adhesion of the hydrogel was lowered. Comparative Example 3 exhibited a very good moisturizing feeling, but the adhesion, stiffness, and stability thereof were relatively inappropriate for cosmetics. Similar to Comparative Example 2, in the case of Comparative Example 3, the moisturizing feeling was improved by the filling solution, but excessive filling had a negative effect on the stiffness, stability and adhesion of the hydrogel.

The hydrogel of Comparative Example 4 exhibited good moisturizing feeling, stiffness and stability, but the adhesion thereof was moderate. In the case of Comparative Example 4 which included no filling solution, a large amount of syneresis occurred for the reasons described above with respect to Comparative Example 1, and thus the water content decreased compared to those of the other Examples. The reason why the moisturizing feeling was improved is that the porosity of the polymer network structure changed depending on the pH of the hydrogel. As the pH decreased, the affinity of the organic polymer for the solvent increased, and thus the unfolding of the structure of the polymer occurred. In addition, the reason for the reduced adhesion was that more syneresis than that in Comparative Example 1 occurred, but the viscosity of the syneresis liquid was excessively low, and thus slippage of the gel on the skin surface occurred. Thus, it can be confirmed that the thickener of the filling solution improves the adhesion of the hydrogel to the skin by controlling the viscosity of the syneresis liquid.

The hydrogel of Comparative Example 5 exhibited a very good moisturizing feeling, but the adhesion, stiffness rigidity and stability thereof were relatively inadequate for cosmetics. In Comparative Example 5, as in Comparative Examples 2 and 3, swelling of the hydrogel due to an excessive amount of the filling solution occurred, which had a negative effect on the stiffness and stability of the hydrogel, and excessive syneresis had a negative effect on the adhesion of the hydrogel. In addition, since the pH of the hydrogel was low, more syneresis than that in the case of the hydrogel with pH 7.0 occurred, and thus the physical properties of the hydrogel were inferior even though the amount of the filling solution was smaller than that of Comparative Example 3.

Comparative Examples 3 and 5 were relatively inappropriate for cosmetics in terms of adhesion, rigidity and stability, and thus could not be applied to actual patches. Comparative Examples 1 and 4 were not suitable for actual patches because the moisturizing feeling thereof was not excellent, even though the moisturizing feeling and stability thereof were moderate. Comparative Example 3 exhibited moderate adhesion, stiffness and stability, and thus were less suitable for patches. Although the stability of Example 4 was moderate, the hydrogel of Example 4 was able to be applied as a patch because it had very good moisturizing feeling and adhesion and good stiffness.

According to the embodiments of the present disclosure, it is preferable that, in the hydrogel composition consisting of composition A and composition C, the content of composition A is more than 70% w/w and the content of composition C is less than 30% w/w, based on the total weight of the hydrogel. In addition, it is preferable that, in the hydrogel composition consisting of composition B and composition D, the content of composition B is more than 70% w/w and the content of composition D is less than 30% w/w, based on the total weight of the hydrogel. The above contents are only preferred examples, and in some cases, the content of each of compositions C and D may be more than 50% w/w depending on the composition, thickness, and filling method of the hydrogel.

Although the present disclosure has been described in detail with reference to preferred embodiments, but the present disclosure is not limited to the embodiments, and various modifications can be made by those of ordinary skill in the art without departing from the scope of the technical spirit of the present disclosure.

The invention claimed is:
1. A hydrogel patch containing a filling solution for controlling a syneresis pattern, the hydrogel patch containing:
　a hydrogel comprising a phase A consisting of a crosslinking agent and purified water, a phase B consisting of an organic polymer and a polyhydric alcohol, and a phase C consisting of a pH adjusting agent and purified water, wherein according to the pH adjusting agent of the phase C, the hydrogel is classified as a composition A having a neutral to basic pH or a composition B having an acidic pH; and
　a filling solution comprising a phase D consisting of a humectant and purified water, a phase E consisting of a thickener and a polyhydric alcohol, and a phase F consisting of a pH adjusting agent and purified water, wherein according to the pH adjusting agent of the phase F, the filling solution is classified as a composition C having a neutral to basic pH or a composition D having an acidic pH,
wherein:
the organic polymer comprises carrageenan and carob gum;
the crosslinking agent, the carrageenan, the carob gum and the polyhydric alcohol are contained in amounts of more than 0% w/w and less than or equal to 5.0% w/w, 0.1 to 5.0% w/w, more than 0% w/w and less than or equal to 4.0% w/w, and 15.0 to 30.0% w/w, respectively, based on the total weight of the hydrogel;
the thickener of the phase E is contained in an amount of more than 0% w/w and less than or equal to 5.0% w/w based on the total weight of the hydrogel;

the thickener of the phase E reduces a difference in osmotic pressure between the filling solution and the hydrogel by reducing a viscosity of the filling solution; and the crosslinking agent in the hydrogel is any one or a mixture of two or more selected from cationic inorganic compounds containing an alkali metal salt or an alkaline earth metal salt.

2. The hydrogel patch of claim 1, which is composed of the composition A and the composition C, wherein a content of the composition A is more than 70% w/w based on the total weight of the hydrogel patch, and a content of the composition C is less than 30% w/w based on the total weight of the hydrogel patch.

3. The hydrogel patch of claim 1, which is composed of the composition B and the composition D, wherein a content of the composition B is more than 70% w/w based on the total weight of the hydrogel patch, and a content of the composition D is less than 30% w/w based on the total weight of the hydrogel patch.

4. The hydrogel patch of claim 1, wherein the pH adjusting agent is arginine as a basic pH adjusting agent, or citric acid as an acidic pH adjusting agent.

5. The hydrogel patch of claim 1, wherein the organic polymer in the hydrogel further comprises one or more selected from guar gum, cellulose gum, and polyacrylate, and the polyhydric alcohol is any one or a combination of two or more selected from glycerin, dipropylene glycol, butylene glycol, propanediol and pentylene glycol.

6. The hydrogel patch of claim 5, wherein the polyhydric alcohol is a combination of glycerin and butylene glycol, which comprises, based on the total weight of the hydrogel, 5.0 to 20.0% w/w of glycerin and more than 0% w/w and less than or equal to 10.0% w/w of butylene glycol, and the combination of glycerin and butylene glycol is contained in an amount of 15.0% w/w to 30.0% w/w based on the total weight of the hydrogel.

7. The hydrogel patch of claim 1, wherein the thickener in the filling solution is one or more selected from carbomer, xanthan gum, acrylate/C10-30 alkyl acrylate crosspolymer, ammonium acryloyldimethyltaurate/Vpicopolymer, hydroxyethyl acrylate/sodium acryloyldimethyl taurate copolymer, hydroxyethyl cellulose, guar gum, carob gum, and cellulose gum, and the humectant in the filling solution is one or a combination of two or more selected from the group consisting of allantoin, betaine, glucose, sorbitol, glycerin, butylene glycol, propanediol, and dipropylene glycol.

* * * * *